United States Patent
Wang et al.

(10) Patent No.: US 8,252,571 B2
(45) Date of Patent: Aug. 28, 2012

(54) PREPARATION OF SOLVENT-BORNE POLYMERIC BIOACTIVE COATINGS

(75) Inventors: Ping Wang, North Oaks, MN (US); Songtao Wu, St. Paul, MN (US); Hongfei Jia, Ann Arbor, MI (US); Masahiko Ishii, Okazaki (JP); Xiaodong Tong, St. Paul, MN (US); Minjuan Zhang, Ann Arbor, MI (US)

(73) Assignees: Toyota Motor Engineering & Manufacturing North America, Inc., Erlanger, KY (US); Toyota Motor Corporation, Toyota (JP); Regents of the University of Minnesota, Minneapolis, MN (US)

( * ) Notice: Subject to any disclaimer, the term of this patent is extended or adjusted under 35 U.S.C. 154(b) by 517 days.

(21) Appl. No.: 12/434,320

(22) Filed: May 1, 2009

(65) Prior Publication Data

US 2010/0279376 A1    Nov. 4, 2010

(51) Int. Cl.
*C12N 9/00* (2006.01)
*C08F 283/00* (2006.01)
(52) U.S. Cl. ...................... 435/183; 525/54.1
(58) Field of Classification Search .................. 435/183; 524/54.1
See application file for complete search history.

(56) References Cited

U.S. PATENT DOCUMENTS

| | | | |
|---|---|---|---|
| 4,094,744 | A | 6/1978 | Hartdegen et al. |
| 4,098,645 | A | 7/1978 | Hartdegen et al. |
| 4,195,127 | A | 3/1980 | Hartdegen et al. |
| 4,195,129 | A | 3/1980 | Fukui et al. |
| 5,914,367 | A | 6/1999 | Dordick et al. |
| 6,291,582 | B1 | 9/2001 | Dordick et al. |
| 6,599,627 | B2 | 7/2003 | Yeo et al. |
| 6,855,746 | B2 | 2/2005 | Yoshitake et al. |
| 6,905,733 | B2 | 6/2005 | Russell et al. |

FOREIGN PATENT DOCUMENTS

WO   WO-2009/155115 A2 * 12/2009

OTHER PUBLICATIONS

Novick, S. et al., Protein-containing hydrophobic coatings and films, *Biomaterials*, 23: 441-448, 2002.
Drevon, G. et al., High-Activity Enzyme-Polyurethane Coatings, *Biotechnology and Bioengineering*, 79(7): 785-794, Sep. 30, 2002.

* cited by examiner

*Primary Examiner* — Karen Cochrane Carlson
(74) *Attorney, Agent, or Firm* — Gifford, Krass, Sprinkle, Anderson & Citkowski, P.C.

(57) ABSTRACT

Processes for preparation of a protein-polymer composite material are provided according to embodiments of the present invention which include providing an admixture of a polymer resin, a surfactant and a non-aqueous organic solvent. An aqueous solution containing bioactive proteins and substantially free of surfactant is mixed with the admixture. The emulsion is mixed with a crosslinker to produce a curable composition. The curable composition is cured, thereby producing the protein-polymer composite material.

23 Claims, 7 Drawing Sheets

PREPARATION OF SOLVENT-BORNE POLYMERIC BIOACTIVE COATINGS

FIELD OF THE INVENTION

The present invention relates generally to processes for preparing coating compositions including bioactive substances. In specific embodiments, the invention relates to processes for preparing protein-polymer composite materials for use in form of thin film coatings.

BACKGROUND OF THE INVENTION

Bioactive proteins are potentially useful in various applications. However, there is a continuing need for processes of preparing materials including bioactive substances, particularly protein-polymer composite materials.

SUMMARY OF THE INVENTION

Methods according to embodiments of the present invention are provided which include formation of fine emulsion solution that contains bioactive proteins dispersed in a continuous phase containing polymerizable ingredients, such that the proteins are entrapped and crosslinked with polymer upon the formation of the polymer network. The crosslinking of at least some of the protein to the polymer network along with the confinement of the protein in the polymer provides long-lasting activity of the protein ingredient in a coating formed using methods and materials described herein.

A process for preparation of a protein-polymer composite material is provided according to embodiments of the present invention which includes providing an admixture of a polymer resin, a surfactant and a non-aqueous organic solvent. An aqueous solution containing bioactive proteins and substantially free of surfactant, is mixed with the admixture, thereby producing an emulsion. The emulsion is mixed with a crosslinker to produce a curable composition; and the curable composition is cured to produce the protein-polymer composite material.

A process for preparation of a protein-polymer composite material is provided according to embodiments of the present invention which includes providing an admixture of a hydroxyl-functionalized acrylate resin, a surfactant and a non-aqueous organic solvent. An aqueous solution containing bioactive proteins and substantially free of surfactant, is mixed with the admixture, thereby producing an emulsion. The emulsion is mixed with a polyisocyanate crosslinker to produce a curable composition; and the curable composition is cured to produce the protein-polymer composite material.

The bioactive proteins included in the protein-polymer composite are selected according to the desired properties of the protein-polymer composite and examples of included bioactive proteins include, but are not limited to, one or more types of enzymes, lectins, antibodies and receptors.

Optionally, one or more additives can be included in the admixture, the aqueous solution, the emulsion, and/or the curable composition.

In embodiments of the present invention, the average particle size of bioactive protein particles in the protein-polymer composite material is less than 10 μm (average diameter) such as in the range of 1 nm to 10 μm, inclusive.

Processes according to further embodiments of the present invention for preparation of a protein-polymer composite material are provided which include providing an admixture of a hydroxyl-functionalized acrylate resin, a surfactant and a solvent which has a log P in the range of −0.5-2, inclusive. An aqueous solution containing bioactive proteins and substantially free of surfactant, is mixed with the admixture, thereby producing an emulsion. The emulsion is mixed with a polyisocyanate crosslinker to produce a curable composition; and the curable composition is cured to produce the protein-polymer composite material.

Processes for preparation of a two component solvent-borne protein-polymer composite material according to a further embodiment of the present invention include providing an admixture of a polymer resin and a non-aqueous organic solvent and mixing an aqueous solution containing bioactive proteins with the admixture, wherein the aqueous solution is substantially free of surfactant, to produce a first component. A second component including a crosslinker is mixed with the first component to produce a curable composition. The curable composition is cured to produce a protein-polymer composite material of the present invention.

A protein-polymer composite material according to embodiments of the present invention includes bioactive proteins dispersed in a two component solvent-borne polymer resin. The bioactive proteins are dispersed such that the average particle size of bioactive protein particles in the protein-polymer composite material is less than 10 μm (average diameter) such as in the range of 1 nm to 10 μm, inclusive.

BRIEF DESCRIPTION OF THE DRAWINGS

FIGS. 1A and 1B are illustrations of flow diagrams of processes according to embodiments of the present invention;

FIG. 2 is a schematic illustration of incorporation of bioactive proteins by covalent bonding of the bioactive proteins and the polymer or crosslinker as well as by physical entrapment of the proteins;

FIG. 3 is a graph showing thermostability of native α-amylase;

FIG. 4 is a graph showing thermostability of α-amylase incorporated in a two component solvent-borne polyurethane (2K SB PU) coating produced according to embodiments of the present invention;

FIG. 5 is a graph illustrating long-term stability of incorporated α-amylase in different types of polyurethane (PU) coatings at room temperature.

FIG. 6 is a confocal laser scanning microscopic image of 2K SB PU containing α-amylase at a depth of ~2 μm from the top surface.

DETAILED DESCRIPTION OF THE INVENTION

Processes for preparation of protein-polymer composite materials are provided according to embodiments of the present invention. Protein-polymer composite materials according to the present invention are useful in numerous applications, including coatings, such as for biosensors, antifouling surfaces and biocatalytic devices.

Processes for preparation of protein-polymer composite materials are provided according to embodiments of the present invention which include use of aqueous solutions of bioactive proteins and non-aqueous organic solvent-borne polymers to produce bioactive organic solvent-borne protein-polymer composite materials. These inventive processes are also referred to as "direct dispersion" processes herein.

Processes provided according to embodiments of the present invention are generally illustrated in the flow diagram shown in FIGS. 1A and 1B. As indicated in FIG. 1A, an aqueous solution of a bioactive protein, 10, and an admixture, 20, of a polymer resin and an organic solvent, are mixed to produce a curable protein-polymer composition, 40. Optionally, a crosslinker, 30, is present in the curable protein-polymer composition, 40, depending on the polymer resin used and the curing modality selected. Curing of the composition is performed to produce a cured protein-polymer composite material, 50.

Figure 1A:
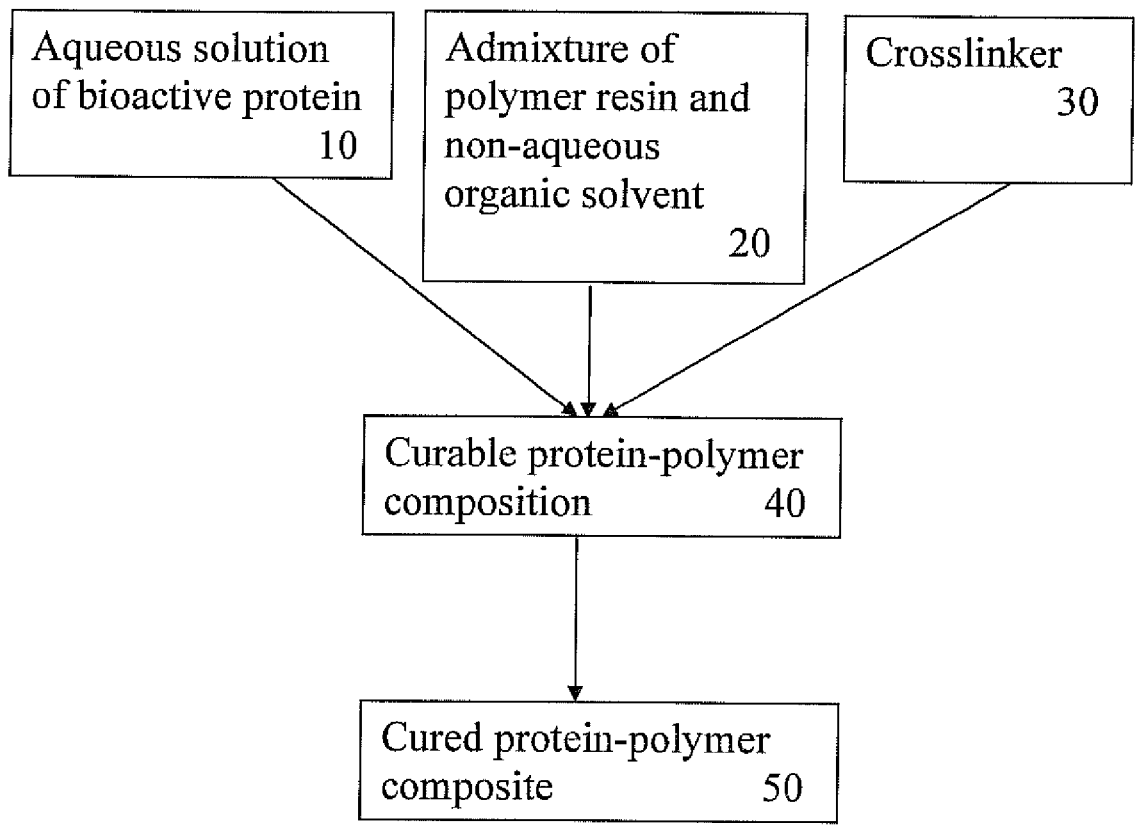
Figure 1B:
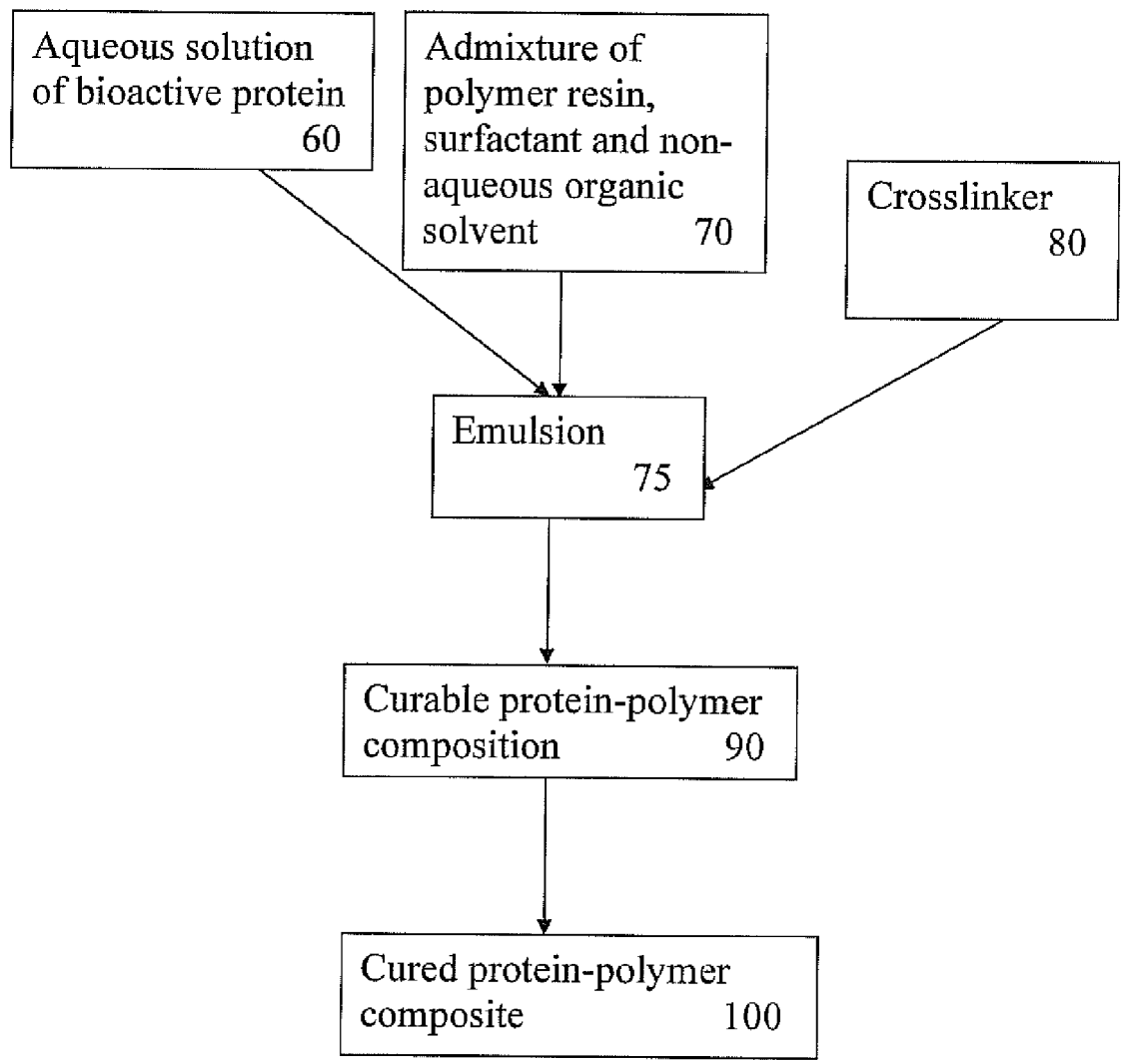

In a preferred embodiment, shown in FIG. 1B, an aqueous solution of a bioactive protein, 60, and an admixture, 70, of a polymer resin, surfactant and a non-aqueous organic solvent, are mixed to produce an emulsion, 75. A crosslinker, 80, is added to the emulsion, 75, depending on the polymer resin used and the curing modality selected, producing a curable protein-polymer composition, 90. The curable protein-polymer composition 90 is cured to produce a protein-polymer composite material, 100.

Processes for preparation of protein-polymer composite materials according to embodiments of the present invention are characterized by dispersion of bioactive proteins in solvent-borne resin prior to curing and in the composite materials, in contrast to forming large aggregates of the bioactive proteins which diminish the functionality of the bioactive proteins and protein-polymer composite materials. In embodiments of the present invention, bioactive proteins are dispersed in the protein-polymer composite material such that the bioactive proteins are unassociated with other bioactive proteins and/or form relatively small particles of associated proteins. Thus, in embodiments, the average particle size of bioactive protein particles in the protein-polymer composite material is less than 10 µm (average diameter) such as in the range of 1 nm to 10 µm, inclusive.

Curable protein-polymer compositions according to embodiments of the present invention are two-component solvent-borne (2K SB) compositions and the two components are mixed shortly before use, for instance, application of the curable protein-polymer composition to a substrate to form a bioactive coating such as a bioactive clear coat. Generally described, the first component contains a crosslinkable polymer resin and the second component contains a crosslinker. Thus, for example, referring to FIG. 1B, the emulsion 75 is a first component containing a crosslinkable resin and the crosslinker 80 is a second component, mixed together to produce the curable protein-polymer composition.

A polymer resin included in processes and compositions of the present invention can be any film-forming polymer useful in coating compositions, such as clear coat compositions. Such polymers illustratively include, aminoplasts, melamine formaldehydes, carbamates, polyurethanes, polyacrylates, epoxies, polycarbonates, alkyds, vinyls, polyamides, polyolefins, phenolic resins, polyesters, polysiloxanes; and combinations of any of these or other polymers.

In particular embodiments, a polymer resin included in a curable composition is crosslinkable. For example, a crosslinkable polymer has a functional group characteristic of a crosslinkable polymer. Examples of such functional groups illustratively include acetoacetate, acid, amine, carboxyl, epoxy, hydroxyl, isocyanate, silane, and vinyl.

A crosslinking agent is optionally included in the curable composition. The particular crosslinker selected depends on the particular polymer resin used. Non-limiting examples of crosslinkers include compounds having functional groups such as isocyanate functional groups, epoxy functional groups, aldehyde functional groups, and acid functionality.

In particular embodiments of processes for forming protein-polyurethane composite materials, a polymer resin included in processes and compositions of the present invention is a hydroxyl-functional acrylic polymer and the crosslinker is a polyisocyanate.

A polyisocyanate, preferably a diisocyanate is a crosslinker reacted with the hydroxyl-functional acrylic polymer according to embodiments of the present invention. Aliphatic polyisocyanates are preferred polyisocyanates used in processes for making protein-polymer composite materials for clearcoat applications such as in automotive clearcoat applications. Non-limiting examples of aliphatic polyisocyanates include 1,4-butylene diisocyanate, 1,4-cyclohexane diisocyanate, 1,2-diisocyanatopropane, 1,3-diisocyanatopropane, ethylene diisocyanate, lysine diisocyanate, 1,4-methylene bis(cyclohexyl isocyanate), diphenylmethane 4,4'-diisocyanate, an isocyanurate of diphenylmethane 4,4'-diisocyanate, methylenebis-4,4'-isocyanatocyclohexane, 1,6-hexamethylene diisocyanate, an isocyanurate of 1,6-hexamethylene diisocyanate, isophorone diisocyanate, an isocyanurate of isophorone diisocyanate, p-phenylene diisocyanate, toluene diisocyanate, an isocyanurate of toluene diisocyanate, triphenylmethane 4,4',4"-triisocyanate, tetramethyl xylene diisocyanate, and meta-xylene diisocyanate.

The term "bioactive protein" as used herein refers to proteins having activity to specifically interact with another substance, such as a ligand, drug, substrate, antigen, or hapten. Bioactive proteins include, but are not limited to, antibodies, lectins, ligand receptors and enzymes. Assays for proteins having activity to specifically interact with another substance include well-known methods such as ELISA, receptor binding assays and enzyme activity assays.

Bioactive proteins selected for inclusion in a particular protein-polymer composite material depend on the intended application of the material and one of skill in the art will be able to select one or more appropriate bioactive proteins.

Protein-polymer composite materials including one or more types of enzyme are provided according to embodiments of the present invention. The term "enzyme" as used herein refers generally to proteins having activity to catalyze a biochemical reaction. Enzymes are generally described according to standardized nomenclature as Enzyme Commission (EC) numbers EC1, oxidoreductases; EC2, transferases; EC3, hydrolases; EC4, lyases; EC5, isomerases; or EC6, ligases. Enzymes in any of these categories can be included in a protein-polymer composite material according to embodiments of the present invention.

In particular embodiments, an included enzyme is a hydrolase, such as a glucosidase, peptidase, or lipase. Non-limiting examples of particular glucosidases include amylase, chitinase and lysozyme. Non-limiting examples of particular peptidases include trypsin, chymotrypsin, thermolysin, subtilisin, papain, elastase, and plasminogen. Non-limiting examples of lipases include pancreatic lipase and lipoprotein lipase.

Bioactive proteins can be obtained from commercial sources, isolated from natural sources such as an organism or cell that produces the bioactive protein or can be synthesized using well-known chemical and/or recombinant methodology.

Bioactive proteins are included in composite materials according to embodiments of the present invention in amounts ranging from 0.1-50% weight percent of the total weight of the composite material composition.

Curing modalities are those typically used for conventional curable polymer compositions.

Protein-polymer composite materials produced by embodiments of processes of the present invention are optionally thermoset protein-polymer composite materials.

For example, thermal curing is used in particular embodiments. A thermal polymerization initiator is optionally included in a curable composition according to embodiments of the present invention. Thermal polymerization initiators include free radical initiators such as organic peroxides and azo compounds. Examples of organic peroxide thermal initiators include benzoyl peroxide, dicumylperoxide, and lauryl peroxide. An exemplary azo compound thermal initiator is 2,2'-azobisisobutyronitrile.

Conventional curing temperatures and curing times can be used in processes according to embodiments of the present invention. For example, the curing time at specific temperatures, or under particular curing conditions, is determined by the criteria that the cross-linker functional groups are reduced to less than 5% of the total present before curing. Cross-linker functional groups can be quantitatively characterized by FT-IR or other suitable method. For example, the curing time at specific temperatures, or under particular curing conditions, for a polyurethane protein-polymer composite of the present invention can be determined by the criteria that the cross-linker functional group NCO is reduced to less than 5% of the total present before curing. The NCO group can be quantitatively characterized by FT-IR. Additional methods for assessing the extent of curing for particular resins are well-known in the art.

Curing may include evaporation of a solvent in particular embodiments.

Optionally, a curable composition is cured by exposure to actinic radiation, such as ultraviolet, electron beam, microwave, visible, infrared, or gamma radiation.

Further embodiments of processes of the present invention include addition of one or more additives for modifying the properties of the protein-polymer composite material and/or the admixture of organic solvent and polymer resin, the aqueous bioactive protein solution, the emulsion, and/or the curable composition. Illustrative examples of such additives include a UV absorbing agent, a plasticizer, a wetting agent, a preservative, a surfactant, a lubricant, a pigment, a filler and an additive to increase sag resistance.

As noted above, in preferred embodiments, a process of the present invention includes an admixture of a polymer resin, a surfactant and a non-aqueous organic solvent, mixed to produce an emulsion. The term "surfactant" refers to a surface active agent that reduces the surface tension of a liquid in which it is dissolved, or that reduces interfacial tension between two liquids or between a liquid and a solid.

Surfactants used can be any of a variety of surfactants including amphoteric, silicone-based, fluorosurfactants, anionic, cationic and nonionic such as described in K. R. Lange, Surfactants: A Practical Handbook, Hanser Gardner Publications, 1999; and R. M. Hill, Silicone Surfactants, CRC Press, 1999. Examples of anionic surfactants include alkyl sulfonates, alkylaryl sulfonates, alkyl sulfates, alkyl and alkylaryl disulfonates, sulfonated fatty acids, sulfates of hydroxyalkanols, sulfosuccinic acid esters, sulfates and sulfonates of polyethoxylated alkanols and allcylphenols. Examples of cationic surfactants include quaternary surfactants and amineoxides. Examples of nonionic surfactants include alkoxylates, alkanolamides, fatty acid esters of sorbitol or manitol, and alkyl glucamides. Examples of silicone-based surfactants include siloxane polyoxyalkylene copolymers.

In preferred embodiments of inventive processes, no surfactant is intentionally added to the aqueous bioactive protein solution and the aqueous bioactive protein solution is substantially free of surfactant. The term "substantially free" refers to the total absence or near-total absence of surfactant in the aqueous bioactive protein solution.

Components used in processes according to embodiments of the present invention are used in amounts described herein, although more or less can be used.

A polymer resin, or mixture of polymer resins, is present in amounts in the range of about 10-90 weight % of the admixture of the polymer resin or polymer resins, solvent and surfactant. In embodiments of the present invention, a polymer resin, or mixture of polymer resins, is present in amounts in the range of about 20-60 weight % of the admixture. A solvent used as a diluent of the polymer resin or resins is typically present in amounts in the range of about 1-50 weight % of the admixture. In embodiments of the present invention, a solvent used as a diluent of the polymer resin or resins is present in amounts in the range of about 2-30 weight % of the admixture. A surfactant is typically present in amounts in the range of about 0.1-5 weight % of the admixture. In embodiments of the present invention, a solvent used as a diluent of the polymer resin or resins is present in amounts in the range of about 0.2-4 weight % of the admixture.

A polymer resin, or mixture of polymer resins, is present in amounts in tie range of about 10-90 weight % of the curable composition. In embodiments of the present invention, a polymer resin, or mixture of polymer resins, is present in amounts in the range of about 20-60 weight % of the curable composition. A solvent used as a diluent of the polymer resin or resins is typically present in amounts in the range of about 1-50 weight % of the curable composition. In embodiments of the present invention, a solvent used as a diluent of the polymer resin or resins is present in amounts in the range of about 2-30 weight % of the curable composition. One or more crosslinkers is present in the curable composition depending on the resin used and the curing modality, in amounts in the range of about 1-30 weight % of the curable composition.

A surfactant added to the admixture of polymer resin or resins and solvent

In particular embodiments, a non-aqueous organic solvent having a log P in the range of –0.5-2, inclusive, is used in processes according to the present invention. In embodiments of the present invention, a non-aqueous organic solvent having a log P in the range of –0.5-2, inclusive is used as a diluent for a polymer resin, for example, to adjust the viscosity of the polymer resin.

The term "log P" refers to the partition coefficient of a substance. The log P of a substance is the base ten logarithm of the ratio of solubility of the substance in n-octanol to solubility of the substance in water. Log P values for many organic solvents are known, for example as described in Leo A, Hansch C, and Elkins D (1971). "Partition coefficients and their uses". *Chem Rev* 71 (6): 525-616. Log P values can also be calculated as described, for example, in Sangster, James (1997). *Octanol-Water Partition Coefficients: Fundamentals and Physical Chemistry, Vol. 2 of Wiley Series in Solution Chemistry*. Chichester: John Wiley & Sons Ltd.

Table 1 shows correlation of log P values with retention of incorporated bioactive protein activity and polyacrylate polyol resin compatibility.

TABLE 1

Solvent compatibility with polyacrylate polyol polymer resins, enzyme activity and stability

| Solvent | Log P | Compatible with resins | Initial specific activity (Unit/cm$^2$) | Half life of coating incubated at 103° C. (hours)* |
|---|---|---|---|---|
| Acetone | −0.23 | Yes | 1.75 | 30 |
| Methyl ethyl ketone | 0.29 | Yes | 1.48 | 59 |
| Ethyl acetate | 0.7 | Yes | 1.32 | 75 |

TABLE 1-continued

Solvent compatibility with polyacrylate polyol polymer resins, enzyme activity and stability

| Solvent | Log P | Compatible with resins | Initial specific activity (Unit/cm$^2$) | Half life of coating incubated at 103° C. (hours)* |
|---|---|---|---|---|
| Methyl isobutyl ketone | 1.31 | Yes | 1.40 | 93 |
| Butyl acetate | 1.7 | Yes | 1.70 | 154 |
| Toluene | 2.5 | Yes | 1.56 | 14 |
| Hexane | 3.5 | No | N/A | N/A |
| Isooctane | 4.5 | No | N/A | N/A |

*Coatings were cured by exposure to 80° C. for 30 minutes and then room temperature for one week before incubation in an oven at 103° C. to evaluate stability of the enzyme in the protein-polymer composite materials.

This relationship shows that bioactive proteins incorporated into solvent-borne protein-polymer composite materials had a similar initial specific activity within a broad range of solvents. However, in terms of stability, solvents having log P values in range of −0.5-2, inclusive, are used in processes described herein and allow for enzyme incorporation into solvent-borne coatings with optimum enzyme stability as shown by half-life times at 103° C. Solvents with log P 3.5 and higher, such as hexane and isooctane, are not compatible with the polyacrylate polyol resins used in embodiments of processes of making two component solvent-borne (2K SB) polymer-protein composites of the present invention.

While preferred embodiments of processes according to the present invention include use of a non-aqueous organic solvent having a log P in the range of −0.5-2, inclusive, solvents having a lower or higher log P could also be used if they are compatible with resins and bioactive proteins.

Non-limiting examples of solvents having log P values ranging from −0.5 to 2, inclusive, include methyl ethyl ketone (0.29), ethyl acetate (0.7), methyl isobutyl ketone (1.31), butyl acetate (1.7) and other solvents listed in Table 2.

A non-aqueous organic solvent having a log P in the range of −0.5-2 inclusive, can be any such solvent compatible with polymer resins and not substantially reactive with a selected crosslinker to be used in a process of the present invention. Examples of non-aqueous organic solvents incompatible with polyacrylate polyol polymer resins and polyisocyanate crosslinkers are aliphatic hydrocarbons and non-aqueous organic solvents having hydroxyl and/or amino groups. Thus, in preferred embodiments, aliphatic hydrocarbon non-aqueous organic solvents and non-aqueous organic solvents having hydroxyl and/or amino groups are excluded as not compatible with polymer resins used in inventive processes.

TABLE 2

Solvents having log P values in the range of −0.5-2

| solvent | Log P |
|---|---|
| Acetone | −0.23 |
| butanone | 0.29 |
| ethyl acetate | 0.68 |
| pentanone | 0.8 |
| cyclohexanone | 0.96 |
| methyl propionate | 0.97 |
| propylacetate | 1.2 |
| ethyl chloride | 1.3 |
| hexanone | 1.3 |
| methyl cyclohexanone | 1.5 |
| benzyl acetate | 1.6 |
| butyl acetate | 1.7 |

It is a surprising finding of the present invention that protein-polymer composite materials retain bioactive protein activity when the curable composition is exposed to elevated temperatures, such as a temperature over 37° C., wherein the temperature is compatible with curing the polymer component included in the composite. In general, it has been believed that exposure of bioactive proteins to temperatures over 37° C. contributes to loss of bioactivity, for instance due to denaturation of the proteins. Without wishing to be bound by theory, it is believed that exposure of the curable composition to a temperature over 37° C. increases and/or accelerates covalent bonding of the bioactive proteins and the polymer or crosslinker. It is known that enzymes tend to denature at high temperature, if no method is provided to prohibit this process. However, it is found that the curing process at high temperature, such as 80° C. for 30 minutes as described in Examples herein, exerts insignificant influence on the incorporated enzymatic activity, indicating the faster formed polymeric matrix at high temperature contributes to the stabilization of the incorporated enzyme via multi-point linkages and confinement. The faster evaporation rate of unfavored solvents at high temperature might also contribute to enzyme activity retention.

Thus, in particular embodiments, the curable composition is exposed to a temperature over 37° C., for a period of time sufficient to decrease leaching of bioactive proteins from the cured composition. Leaching is measured by well-known methods such as those described in the Examples herein.

Figure 2:
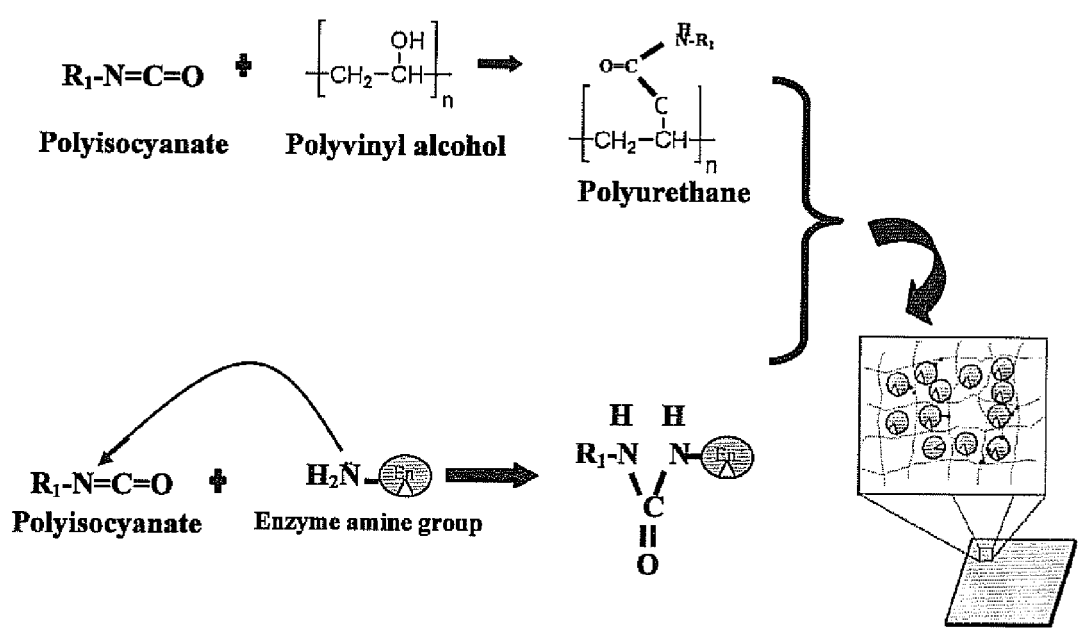

FIG. 2 is a schematic illustration of incorporation of bioactive proteins by covalent bonding of the bioactive proteins and the polymer or crosslinker as well as by physical entrapment of the proteins.

Protein-polymer composite materials are provided according to embodiments of the present invention which include bioactive proteins dispersed in a two component solvent-borne polymer resin. In embodiments of protein-polymer composite materials, the average particle size of bioactive protein particles in the protein-polymer composite material is less than 10 μm (average diameter) such as in the range of 1 nm to 10 μm, inclusive.

In particular embodiments, protein-polymer composite materials produced according to the present invention are protein-polyurethane composite materials.

A curable composition formed by a process described herein is applied to a substrate to form a bioactive coating of protein-polymer composite material according to embodiments of the present invention.

Typically, the coating is applied to produce a coating having a thickness in the range of about 1-500 microns when dry, although coatings thicker or thinner can be used depending on the desired use.

Application of the curable composition is accomplished by any of various methods illustratively including spray coating, dip coating, flow coating, roller coating and brush coating.

A substrate is any of various substrates to which a coating is advantageously applied. For example, a substrate is a sheet material. In a further example, a substrate is a vehicle part, such as a vehicle body panel.

Substrates for use according to the present invention include, but are not limited to, metal substrates, silica, substrates, plastic substrates and glass substrates.

A substrate optionally includes a coating such as a primer, a primer-surfacer, a primer-sealer, a basecoat, an adhesion promoting layer; or a combination of any of these or other surface treatment coatings.

Bioactive coatings of protein-polymer composite material according to embodiments of the present invention provide good adhesion to substrates, protection against environmental insults, protection against corrosion, and further provide bioactive properties of the bioactive protein. Thus, bioactive coatings of protein-polymer composite material according to embodiments of the present invention provide enzyme activity on a substrate useful in numerous applications such as detection of an analyte which is a substrate for the enzyme or a ligand for a receptor, antibody or lectin. In particular embodiments, bioactive coatings provide resistance against staining by enzyme digestion of one or more components of stain producing material.

Embodiments of the invention are illustrated in the following examples. These examples are provided for illustrative purposes and are not considered limitations on the scope of the invention.

Example 1

Direct Dispersion of Enzyme Solution to make Solvent Borne (SB) Polyurethane (PI) Coatings In a typical preparation, the enzyme was first dissolved in DI water at a concentration up to 200 mg/ml. For some enzymes) such as α-amylase (KLEISTASE SD80 from Amano Enzyme Inc.) with large amount of impurities, filtration or centrifugation was required to remove the insoluble solids before use for coating preparation. Hydroxyl-functioned polyacrylate resin (2.1 g of Desmophen A 870 BA from Bayer Corp.) was diluted with a selected solvent at a weight ratio of 2:1 and then mixed with a silicone surfactant polyether modified polydimethylsiloxane (0.1 ml of BYK 333 solution in n-butanol, 17% wt) and enzyme solution (0.6 ml) in a 20-ml glass vial for 1 minute, followed by the addition of 0.8 g of Desmodur N 3600 (Bayer Corp.), hexamethylene diisocyanate, and mixing for another 1 minute. Coating was formed by applying the mixed composition onto a pre-cleaned aluminum testing panel with a drawdown applicator, and cured first at 80° C. for 30 minutes and then at room temperature for 1 week.

Example 2

Activity Assays for Native and Incorporated Enzymes

The activity of α-amylase was measured using a colorimetric assay based on the detection of sugars (mainly maltose) released from the enzyme-catalyzed decomposition of starch. The substrate solution was first prepared by dissolving potato starch in 20 mM, pH6.9 sodium phosphate buffer containing 6.7 mM sodium chloride. In a typical assay, a 10-μl aliquot of α-amylase solution was incubated with 1 ml of substrate solution for 3 minutes at room temperature. Subsequently 1 ml of the 3,5-dinitrosalicylic acid solution is then added. The reaction was stopped by incubation the reaction vial in the boiling water for 15 minutes, followed by cooling in an ice bath. The equivalent of reducing sugar was determined by the absorbance change at 540 nm. One unit of α-amylase activity was defined as 1.0 mg of reducing sugar (calculated from a standard curve previously calibrated against maltose) released from starch in 3 minutes at 25° C., pH 6.9.

The activity of α-amylase in a coating of a protein-polymer composite material was determined in a similar manner except one piece of sample panel coated with α-amylase (1.2×1.9 $cm^2$) prepared in Example 1 was used instead of the enzyme solution. Before every activity test, the coating was extensively rinsed with DI water for at least 5 times to remove physically absorbed enzymes. The rinse solutions were collected, and the protein content in the rinse solution is determined by Bradford reagent to calculate the protein loading in the coating, which was ~50 μg protein/$cm^2$ in the case of α-amylase containing SB PU coating.

Proteolytic activity of thermolysin was determined as follows. Casein solution, 0.65% (w/v) in a sodium phosphate buffer (0.05 M, pH 7.5) buffer, was used as the testing substrate. For native thermolysin, 200 μl of enzyme solution was incubated with 1 ml of substrate solution at 37° C. for 10 min. The reaction was stopped by adding 1 ml of 110 mM of tricholoracetic acid (TCA) solution, and the equivalent of tyrosine in the TCA-soluble fraction was determined at 660 nm using Folin-Ciocalteau reagent. One unit of activity is defined as the amount of enzyme hydrolyzing casein to produce absorbance equivalent to 1.0 μmol of tyrosine per minute at 37° C. The activity of thermolysin in the coatings was determined in a similar manner except one piece of sample plate coated with thermolysin (1.2 cm×1.9 cm) prepared in Example 1 was used instead of the native enzyme solution. Before every activity test, the coatings were extensively rinsed by DI water for at least 5 times to remove physically absorbed enzymes.

Example 3

Effect of Solvent Type on the Surface Activity of Amylase-Containing SB PU Coatings α-Amylase-containing SB PU coatings were prepared following the same procedure as described in Example 1, except that a solvent with different log P values, including acetone (−0.23), methyl ethyl ketone (0.29), ethyl acetate (0.7), methyl isobutyl ketone (1.31) butyl acetate (1.7), toluene (2.7), hexane (3.5) or isooctane (4.5), was used to dilute the resin before the addition of enzyme solution. The performance of the resulting coatings, in terms of surface activity and stability, was evaluated and summarized in Table 1. While little impact was found on the initial surface activity, the solvent type affects enzyme stability. For example, in log P value ranging from −0.23 to 1.7, the half life time of the incorporated α-amylase at 103° C. increased consistently. However, with toluene (log P=2.5) as the diluting solvent, it dropped sharply.

Example 4

Figure 3:
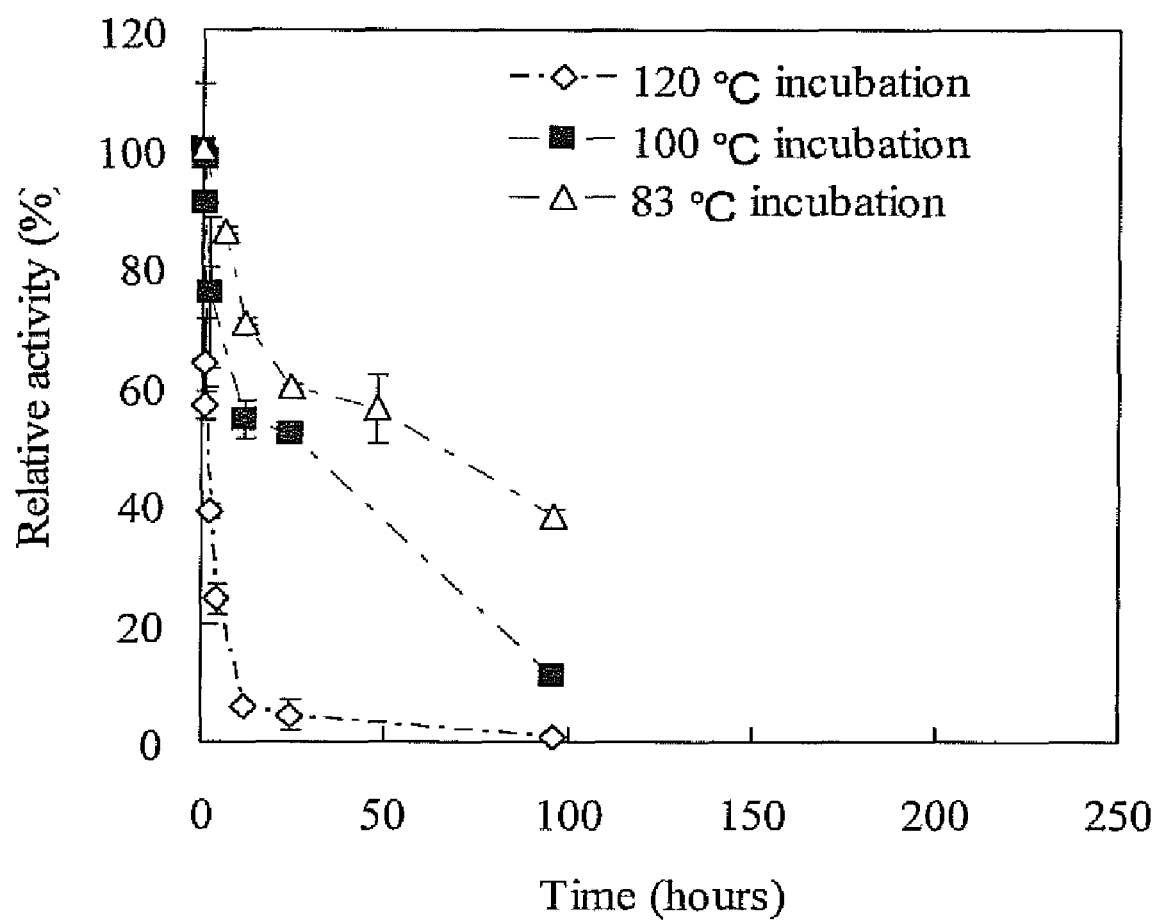
Figure 4:
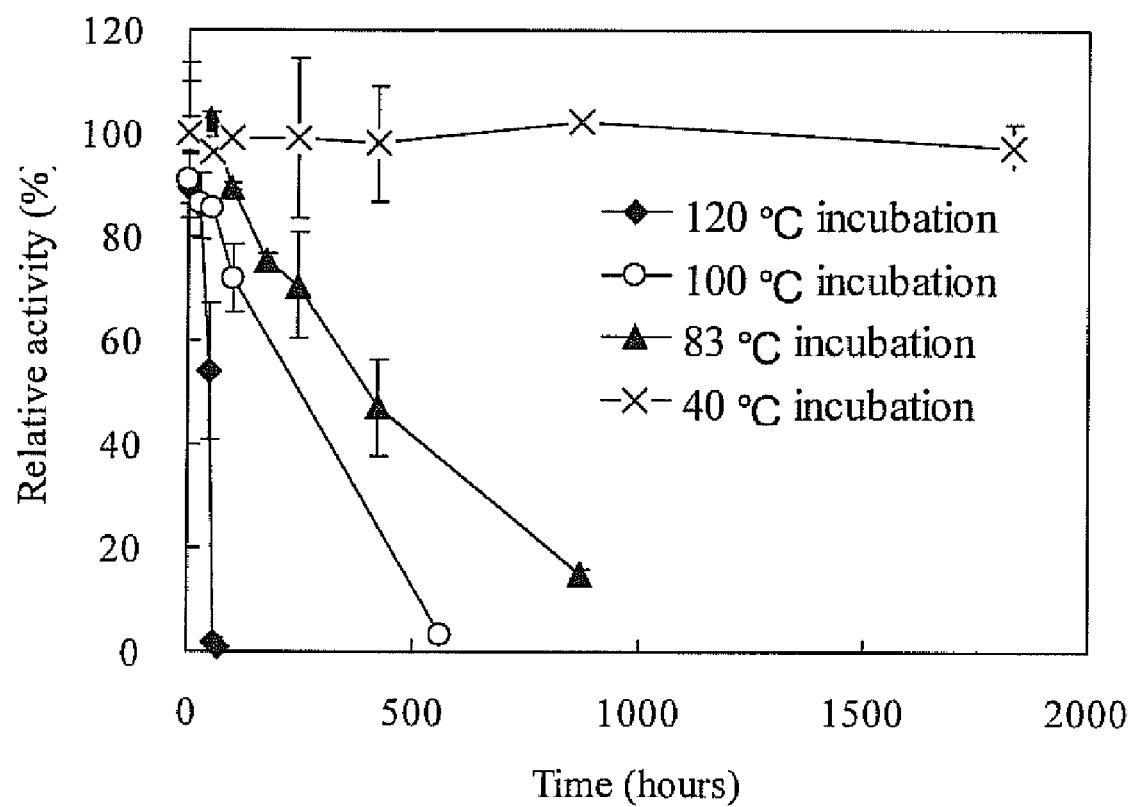

Thermostability of Native and Incorporated α-amylase at Different Temperatures—a Comparative Study The thermostability of α-amylase based bioactive coating prepared as in Example 1 is determined at specified temperatures ranging from room temperature (23° C.) to extremely high temperature of 120° C. After specific periods of aging in a gravity oven, the activity of samples of free enzyme and enzyme-containing coatings were evaluated as in Example 2. The thermostability of native and incorporated α-amylase at different high temperatures ranging from 40, 83, 100 and 120° C. are illustrated in FIGS. 3 and 4, respectively. Compared to native enzyme, the heat-resistance of the enzyme incorporated in SB PU coatings has been greatly enhanced. Estimated half-life times of the incorporated α-amylase were about 460, 200, 31 hours at 83, 100 and 120° C., whereas the half-lives of the freely unbound native counterparts were about 50, 19, 1 hours, respectively. No significant loss of activity for incorporated enzyme is observed while incubating at relatively low temperatures such as 40° C. as shown in FIG. 4 with the estimated half-life as long as 660 days.

Figure 5:
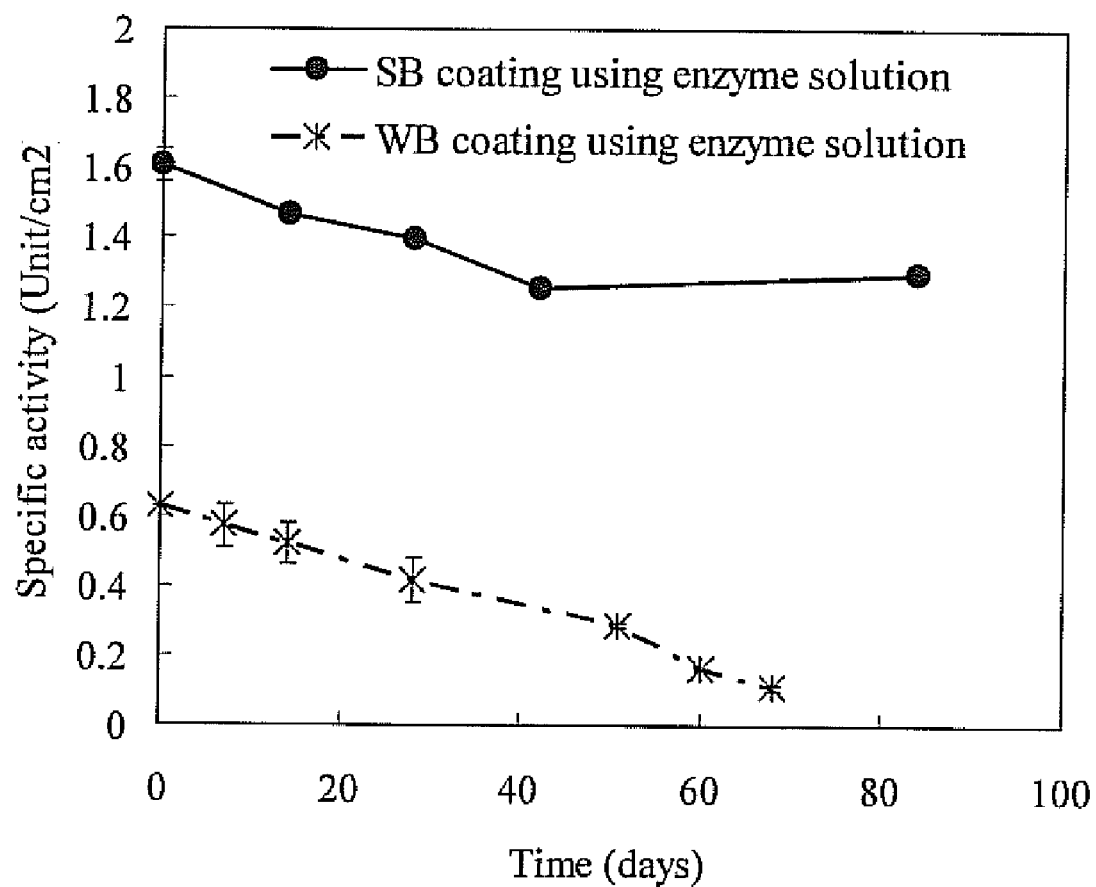

The enzyme in SB coatings afforded better protection to enzyme molecules as compared to water borne (WB) coatings. 2K WB PU coatings containing α-amylase-containing coatings were prepared as follows: 1.5 g of Bayhydrol XP 7093 (from Bayer Corp.) polyester resin was first mixed with equal volume of enzyme solution (20 mg/ml) and 0.36 ml of surfactant BYK 333 (17% w/v in 1-butanol) to form Part A, which was added into Part B, the curing agent-water dispersible diisocyanate (Bayhydrol 302 from Bayer Corp., 0.6 g). After mixing for 1 minute, the coating was prepared and cured following the same procedure for SB coatings as described in Example 1. As shown in FIG. 5, enzymes incorporated into SB PU coatings retained their relative activity over 85% after 3 months, whereas the enzymes in water-borne (WB) PU coatings, showed a constant decrease of activity with a half life of about 50 days.

Example 5

Enzyme Distribution in SB-PU Coating

Figure 6:
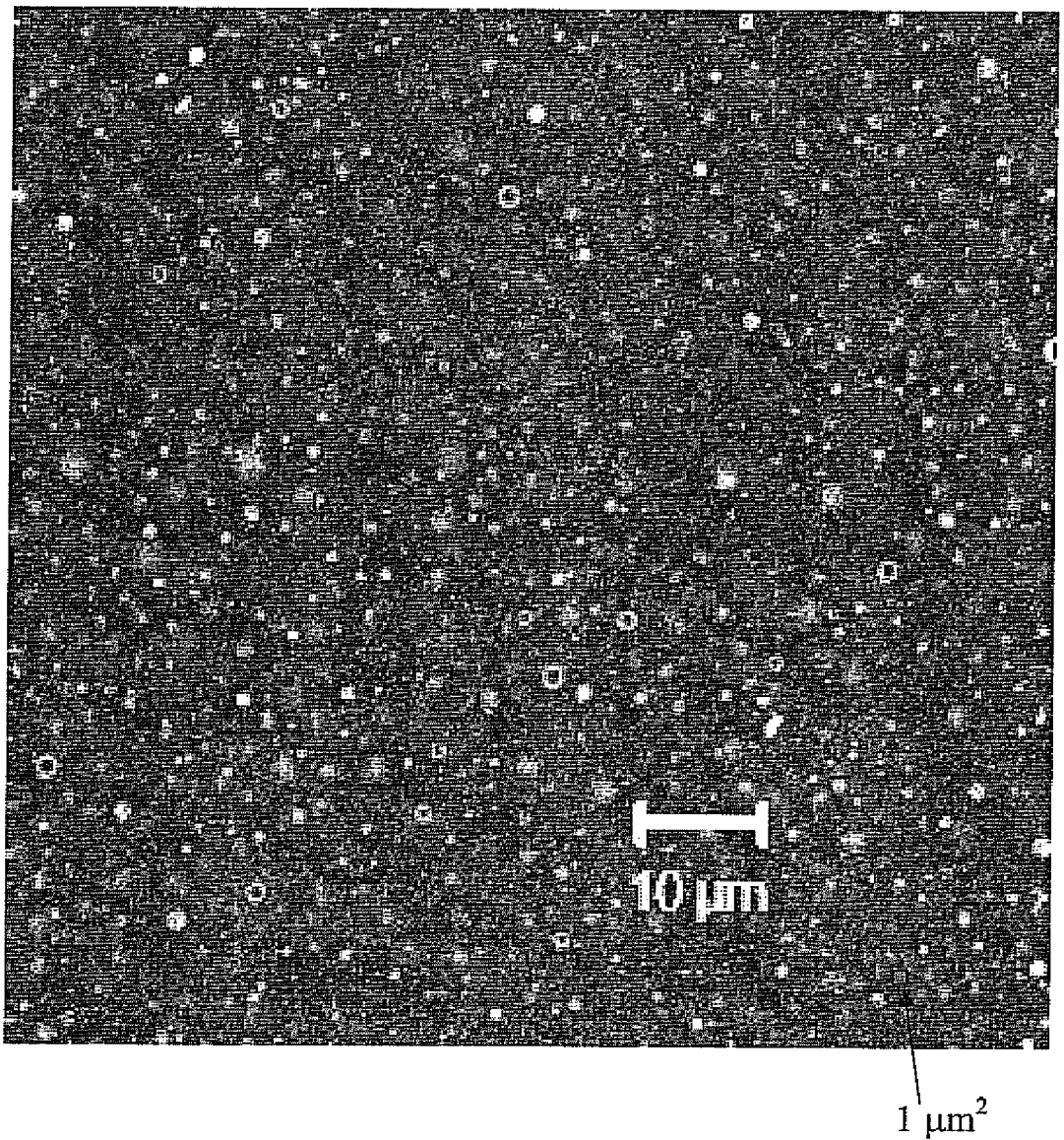

The distribution of α-amylase in the SB PU coatings prepared as described in Example 1 was characterized using fluorescent dye labeling and confocal laser scanning microscopy (CLSM). The enzyme-containing coating was dyed in 5 µM of Oregon Green 488 Maleimide for 16 hrs at 4° C. in dark and then rinsed with pH 7 phosphate buffer for 2 hrs at room temperature. A Prolong Gold anti-fade reagent was used when loading the sample onto the microscope. As control, coatings without enzyme were prepared and examined following the same procedure. Images were taken with an objective lens of 63× with water immersion. The excitation and max emission wavelengths are 488 nm and 524 nm, respectively. As shown in FIG. 6, the enzyme molecules were dispersed in the coating in the form of small particles with size ranging from submicron to a few micrometers.

Any patents or publications mentioned in this specification are incorporated herein by reference to the same extent as if each individual publication is specifically and individually indicated to be incorporated by reference.

The compositions and processes described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A process for preparation of a protein-polymer composite material, comprising:
   providing an admixture of a polymer resin, a surfactant and a non-aqueous organic solvent;
   mixing an aqueous solution containing bioactive proteins with the admixture, wherein the aqueous solution is substantially free of surfactant, to produce an emulsion
   mixing the emulsion with a crosslinker to produce a curable composition; and
   curing the curable composition, thereby producing the protein-polymer composite material.

2. The process of claim 1, wherein the polymer resin is a hydroxyl-functionalized acrylate resin.

3. The process of claim 2, wherein the crosslinker is a polyisocyanate.

4. The process of claim 1, wherein the bioactive protein is an enzyme.

5. The process of claim 1, wherein the bioactive protein is selected from the group consisting of: a lectin, an antibody and a receptor.

6. The process of claim 1, further comprising addition of one or more additives to at least one of: the admixture, the aqueous solution, the emulsion, and the curable composition.

7. The process of claim 1 wherein the average particle size of bioactive protein particles in the protein-polymer composite material is in the range of 1 nm to 10 µm (average diameter), inclusive.

8. A process for preparation of a protein-polymer composite material, comprising:
   providing an admixture of a hydroxyl-functionalized acrylate resin, a surfactant and a solvent, the solvent having a log P in the range of −0.5-2, inclusive;
   mixing an aqueous solution containing a bioactive protein with the admixture, wherein the aqueous solution is substantially free of surfactant, to produce an emulsion;
   mixing the emulsion with a polyisocyanate crosslinker to produce a curable composition; and
   curing the polymerizable composition, thereby producing the composite material.

9. The process of claim 8, wherein the bioactive protein is an enzyme.

10. The process of claim 8, wherein the bioactive protein is selected from the group consisting of: a lectin, an antibody and a receptor.

11. The process of claim 8, further comprising addition of one or more additives to at least one of: the admixture, the aqueous solution, the emulsion, and the curable composition.

12. The process of claim 8 wherein the average particle size of bioactive protein particles in the protein-polymer composite material is in the range of 1 nm to 10 µm (average diameter), inclusive.

13. The process of claim 1, further comprising applying the curable composition to a substrate prior to curing the curable composition.

14. A process for preparation of a protein-polymer composite material, comprising:
   providing an admixture of a polymer resin and a non-aqueous organic solvent;
   mixing an aqueous solution containing bioactive proteins with the admixture, wherein the aqueous solution is substantially free of surfactant, to produce a first component;
   providing a second component comprising a crosslinker;
   mixing the first component and the second component to produce a curable composition; and
   curing the curable composition, thereby producing the protein-polymer composite material.

15. The process of claim 14, wherein the curing comprises thermal curing.

16. The process of claim 14, wherein the curing comprises curing using actinic radiation.

17. The process of claim 14, wherein the bioactive protein is an enzyme.

18. The process of claim 14, wherein the bioactive protein is selected from the group consisting of: a lectin, an antibody and a receptor.

19. The process of claim 14, further comprising addition of one or more additives to at least one of: the admixture, the aqueous solution, the emulsion, and the curable composition.

20. The process of claim 14 wherein the average particle size of bioactive protein particles in the protein-polymer composite material is in the range of 1 nm to 10 μm (average diameter), inclusive.

21. The process of claim 14, further comprising applying the curable composition to a substrate prior to curing the curable composition.

22. A protein-polymer composite material, comprising:

bioactive proteins dispersed in a two component solvent-borne polymer resin, the average particle size of bioactive protein particles in the protein-polymer composite material is in the range of 1 nm to 10 μm (average diameter), inclusive, with the proviso that the bioactive proteins are not ion-paired.

23. A curable protein-polymer composite material, comprising:

bioactive proteins dispersed in a curable two component solvent-borne polymer resin, the average particle size of bioactive protein particles in the protein-polymer composite material is in the range of 1 nm to 10 μm (average diameter), inclusive, with the proviso that the bioactive proteins are not ion-paired.

* * * * *

UNITED STATES PATENT AND TRADEMARK OFFICE
CERTIFICATE OF CORRECTION

PATENT NO. : 8,252,571 B2  
APPLICATION NO. : 12/434320  
DATED : August 28, 2012  
INVENTOR(S) : Wang et al.

Page 1 of 1

It is certified that error appears in the above-identified patent and that said Letters Patent is hereby corrected as shown below:

In the Specification

Col. 6, line 19: replace "in tie range" with --in the range--;

Col. 9, line 20: replace "polyurethane (PI)" with --polyurethane (PU)--.

Signed and Sealed this  
Seventh Day of January, 2014

Margaret A. Focarino  
*Commissioner for Patents of the United States Patent and Trademark Office*